United States Patent [19]

Danree et al.

[11] Patent Number: 4,795,758

[45] Date of Patent: Jan. 3, 1989

[54] 5-[2-(PYRROLIDIN-1-YL)ETHOXY]-P-CYMENE DERIVATIVES, THE PROCESS FOR THE PREPARATION OF THE SAID DERIVATIVES AND DRUGS IN WHICH THE SAID DERIVATIVES ARE PRESENT

[75] Inventors: Bernard Danree, Poissy; Patrick Houziaux, Maule; Jean-Yves Lacolle, Saint-nom-la-Breteche, all of France

[73] Assignee: Societe a Responsabilite Limitee: Institut de Recherches Chimiques et Biologiques Appliquees (I.R.C.E.B.A.), France

[21] Appl. No.: 50,616

[22] Filed: May 15, 1987

[51] Int. Cl.$^4$ .................. A61K 31/40; C07D 295/08
[52] U.S. Cl. ........................ 514/428; 548/575
[58] Field of Search ................. 548/575; 514/428

[56] References Cited

U.S. PATENT DOCUMENTS

| | | | |
|---|---|---|---|
| 2,914,552 | 11/1959 | Hiltmann et al. | 548/575 X |
| 3,205,136 | 9/1965 | Tedeschi | 514/428 X |
| 3,740,397 | 6/1973 | Lafon | 548/575 X |
| 3,767,819 | 10/1973 | Leeming et al. | 514/428 X |
| 3,793,366 | 2/1974 | Krapcho | 548/575 X |

FOREIGN PATENT DOCUMENTS

| | | | |
|---|---|---|---|
| 1248417 | 11/1960 | France | 548/575 |
| 1549152 | 11/1968 | France . | |

OTHER PUBLICATIONS

Wheatley, et al., J. Org. Chem., 23, 568–571.
Goodman et al., "The Pharmacological Basis of Therapeutics", pp. 549–565, Chapter 26 (1970), 4th Ed., The Macmillan Co., London.

*Primary Examiner*—Joseph Paul Brust
*Attorney, Agent, or Firm*—Brumbaugh, Graves, Donohue & Raymond

[57] ABSTRACT

The present invention relates to novel products of the formula:

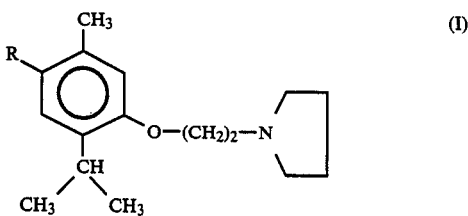

in which R is selected from the group comprising H, OH, —O—COCH$_3$ and —O—CO—(CH$_2$)$_n$—CH$_3$, in which n is between 1 and 8, and the salts of the products of the formula (I) with pharmaceutically acceptable acids.

5 Claims, No Drawings

5-[2-(PYRROLIDIN-1-YL)ETHOXY]-P-CYMENE DERIVATIVES, THE PROCESS FOR THE PREPARATION OF THE SAID DERIVATIVES AND DRUGS IN WHICH THE SAID DERIVATIVES ARE PRESENT

The present invention relates to 5-[2-(pyrrolidin-1-yl)ethoxy]-p-cymene derivatives; it also relates to a process for the preparation of these derivatives and drugs in which the said derivatives are present.

The 5-[2-(pyrrolidin-1-yl)ethoxy]-p-cymene derivatives are the novel products of the formula:

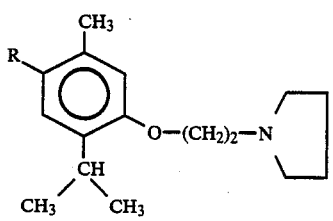

in which R is selected from the group comprising H, OH, OCOCH$_3$ (acetoxy) and OCO(CH$_2$)$_n$CH$_3$, in which n is between 1 and 8 (1 and 8 being included in the definition of n), and the salts of the products of the formula (I) with pharmaceutically acceptable acids.

The process for the preparation of the compounds of the formula (I) consists, in a first stage, in reacting thymol with N-(2-chloroethyl)pyrrolidine hydrochloride; the reaction is performed by phase transfer in a liquid-liquid system in the presence of a catalyst (triethylbenzylammonium chloride); this gives the product of the formula (I) in which R is H. The product of the formula (I) in which the group R is acetyl is prepared in a solvent, such as toluene, and in the presence of 70% perchloric acid, by reacting the product in which R=H with acetic anhydride.

The product of the formula (I) in which the group R is acetoxy is prepared by reacting an oxidizing agent, such as m-chloroperbenzoic acid, with the derivative of the formula (I) in which R is acetyl, the said reaction being performed in a solvent (toluene) in the presence of an acid (trichloroacetic acid).

The product of the formula (I) in which the group R is a hydroxyl group is prepared by saponifying the product in which R is the acetoxy group with a solution of sodium hydroxide.

Finally, the product of the formula (I) in which the group R is OCO(CH$_2$)$_n$CH$_3$ is prepared by esterifying the product in which R is OH with an acid chloride of the formula:

The salts, for example the hydrochlorides, are obtained in a known manner by bringing a solution of the product of the formula (I) into contact with the acid in question (for example by bubbling hydrogen chloride into a solution of the product of the formula (I).

The present invention also relates to drugs which contain at least one product of the formula (I) as the active product; the said drugs can be useful especially in the field of urology.

The non-limiting examples which follow illustrate the processes for the preparation of the products according to the invention.

EXAMPLE 1

Synthesis of 3-[2-(pyrrolidin-1-yl)ethoxy]-p-cymene hydrochloride (B 1007)

1. Preparation of 3-[2-(pyrrolidin-1-yl)ethoxy]-p-cymene

The following are introduced into a 4 liter three-necked flask fitted with a condenser, a pneumatic stirrer and a thermometer;

150.2 g (1 mol) of thymol,
16.68 g of triethylbenzylammonium chloride, and
751 ml of sodium carbonate solution.

1495 ml of methylene chloride are added. The medium is stirred very vigorously.

The addition of 212.76 g of N-(2-chloroethyl)pyrrolidine hydrochloride (1.25 mol) in 70.9 ml of water causes the temperature to rise to 25° C.

The mixture is heated under reflux for 4 hours, with vigorous stirring.

After cooling to room temperature, the organic phase is left to separate out and the sodium carbonate phase is extracted with 2×425 ml of methylene chloride.

The combined organic phases are washed successively with 2 ×350 ml of acidified water (0.25% acetic acid) and then 2 ×700 ml of a saturated aqueous solution of sodium chloride until the washings are neutral. They are then dried over sodium sulfate.

After filtration, the solvent is driven off in vacuo.

This gives 259.57 g of an orange oil.

The crude product is purified by fractional distillation in vacuo (under nitrogen).

184.7 g of a colorless oil are isolated. Boiling point under 0.1 mm Hg: 155–160° C.; perchloric acid/CH$_3$COOH titer: 102.1%.

2. Preparation of the hydrochloride 24.73 g of this oil (0.1 mol) are dissolved in 400 ml of anhydrous ethyl ether. The solution is saturated with a stream of dry HCl gas in an ice bath. The crystals formed are filtered off on a glass frit, washed with anhydrous ethyl ether and then dried over potassium hydroxide at 70° C.

This gives 25.12 g of beige crystals (yield of crude product=88.6%).

After recrystallization from ethyl acetate, 22.22 g of slightly beige crystals are isolated.

The crystals obtained were subjected to elemental analysis (empirical formula C$_{16}$H$_{26}$ClNO), which gave the following results:

|    | calculated | found |
|----|------------|-------|
| C  | 67.70      | 67.69 |
| H  | 9.23       | 9.25  |
| N  | 4.93       | 4.83  |
| Cl | 12.48      | 12.65 |
| O  | 5.63       | 5.76  |

The crystals have a melting point m.p.$_{KB}$ of 157–158° C. and their IR and NMR spectra are consistent with the proposed structure.

EXAMPLE 2

Synthesis of
2-acetyl-5-[2-(pyrrolidin-1-yl)ethoxy]-p-cymene

The 3-[2-(pyrrolidin-1-yl)ethoxy]-p-cymene obtained according to process 1 of Example 1 is used as the starting material; this product was purified beforehand.

247.38 g (1 mol) of this product are dissolved in 1600 ml of toluene and 863 ml of acetic anhydride in a 4 liter three-necked flask fitted with a condenser equipped with an $H_2SO_4$ trap, a thermometer and a dropping funnel. The mixture is stirred and 225.2 ml of 70% perchloric acid are then added dropwise, the temperature being kept below 45° C.

The mixture is stirred for 1 hour at room temperature and then poured into 760 ml of a saturated aqueous solution of NaCl.

After cooling with an ice bath and rendering basic with sodium carbonate solution (pH: 12), the organic phase is separated off and extraction is carried out with 2×300 ml of methylene chloride. The organic phases are combined and washed with acidified water and a saturated aqueous solution of NaCl until the washings are neutral. They are dried over sodium sulfate and filtered and the solvent is driven off in vacuo. This gives 297.3 g of a brown oil with a GC purity of 97% (yield of crude product >100%).

The crude product is then purified by fractional distillation in vacuo (under nitrogen).

196.14 g of a yellow oil are isolated.

The product obtained has a boiling point (under 0.4 mm Hg) of 149°–153° C. and a perchloric acid titer of 98.6% and its IR and NMR spectra are consistent with the proposed structure.

EXAMPLE 3

Synthesis of
2-acetoxy-5-[2-(pyrrolidin-1-yl)ethoxy]-p-cymene
hydrochloride (B 1024)

1. Synthesis of 2-acetoxy-5-[2-(pyrrolidin-1-yl)ethoxy]-p-cymene

The purified oil obtained in Example 2 is used as the starting material.

289.42 g (1 mol) of this product and 1650 ml of toluene are introduced into a 4 liter three-necked flask fitted with a condenser equipped with an $H_2SO_4$ trap, a thermometer and a pneumatic stirrer.

392.13 g (2.4 mol) of trifluoroacetic acid are added in portions, the temperature being kept below 15° C. 258.84 g (1.2 mol) of 80% m-chloroperbenzoic acid are then introduced.

The mixture is kept at 15° C. for 24 h, with stirring. It is then poured into 2130 ml of 5% aqueous ammonia.

The organic phase is separated off by decantation. The aqueous phase is extracted with 2 times 890 ml of toluene. The organic phases are combined and washed with 890 ml of acidified water and then 1180 ml of a saturated aqueous solution of NaCl until the washings are neutral. They are dried over sodium sulfate and filtered and the solvent is driven off in vacuo.

This gives 266.3 g of a brown oil with a GC purity of 97.2% (yield of crude product=87.2%).

2. Synthesis of the hydrochloride 30.54 g (0.1 mol) of this crude oil are dissolved in 210 ml of anhydrous ethyl ether. A stream of dry HCl gas is bubbled into the solution, in an ice bath. The crystals formed are filtered off on a glass frit, washed with anhydrous ethyl ether and then dried over potassium hydroxide at 50° C. in vacuo.

16.74 g of beige crystals are isolated (yield of crude product=49%).

After recrystallization from a 20/1 AcOEt/EtOH mixture, 11.31 g of light beige crystals are obtained.

The said crystals have a melting point m.p.$_{KB}$ of 182°–183° C. and a perchloric acid titer of 100.8% and their IR and NMR spectra are consistent with the proposed structure.

EXAMPLE 4

Synthesis of
2-hydroxy-5-[2-(pyrrolidin-1-yl)ethoxy]-p-cymene
hydrochloride (B 1058)

The purified oil obtained after the first operation of Example 3 is used as the starting material.

30.5 g (0.1 mol) of this oil and 110 ml of ethanol are introduced into a 500 ml conical flask fitted with a condenser and a magnetic stirrer.

110 ml of 1 N sodium hydroxide solution (0.11 mol) are added to this solution and the mixture is stirred for 24 h at room temperature. The ethanol is driven off in vacuo; the residue is taken up with 150 ml of water and extracted with 3 times 180 ml of methylene chloride.

The combined organic phases are washed with a saturated aqueous solution of sodium chloride until the washings are neutral. They are dried over sodium sulfate and the solvent is driven off in vacuo. This gives 25.28 g of an orange oil (yield of crude product=96%).

After crystallization from hot pentane and recrystallization from hexane, 21.54 g of white crystals are isolated which have a melting point m.p.$_{KB}$ of 86°–87° C.

The product obtained was converted to a salt (hydrochloride) by the following procedure:

13.16 g (0.05 mol) of purified base are dissolved in 200 ml of anhydrous ethyl ether, with stirring. After a stream of dry HCl gas has been bubbled in, the crystals formed are isolated by filtration on a frit.

After washing with ethyl ether and drying in vacuo at 50° C., 14.54 g of beige crystals are obtained (yield of crude product=97%).

After recrystallization from an AcOEt/EtOH mixture (2/1), 11.1 g of white crystals are isolated.

The said crystals have a melting point m.p.$_{KB}$ of 147°–148° C. and their IR and NMR spectra are consistent with the proposed structure; elemental analysis of these crystals (empirical formula $C_{16}H_{26}ClNO_2$) gave the following results:

|    | calculated | found |
|----|------------|-------|
| C  | 64.09      | 64.08 |
| H  | 8.74       | 8.78  |
| N  | 4.67       | 4.65  |
| Cl | 11.82      | 11.96 |
| O  | 10.67      | 10.86 |

EXAMPLE 5

Preparation of an ester and its hydrochloride

A - Synthesis of 2-butyryloxy-5-[2-(pyrrolidin-1-yl)ethoxy]-p-cymene (R=$CH_3$-$(CH_2)_2$-)

The following are introduced, with stirring, into a 500 ml three-necked flask fitted with a condenser, a pneumatic stirrer and a thermometer:

26.3 g (0.1 mol) of 2-hydroxy-5-[2-(pyrrolidin-1-yl)ethoxy]-p-cymene,
200 ml of benzene and
10.6 g of triethylamine (0.105 mol).

11.2 g (0.105 mol) of butyryl chloride are added to this solution.

The reaction medium is heated at 50° C. for 20 hours.

The progress of the reaction is monitored by gas chromatographic analyses of the medium.

After cooling to room temperature, the reaction mixture is poured into 350 ml of water.

The benzene phase is decanted and countercurrent extraction is carried out on the aqueous phase with 3×250 ml of benzene.

The combined benzene phases are washed with water until the washings are neutral, and dried over sodium sulfate.

After filtration, the solvent is driven off in vacuo.

This gives 31.5 g of a brown oil.

| | |
|---|---|
| Yield of crude product = | 94.5% |
| GC purity = | 99.5% |
| Perchloric acid titer = | 94.3% |
| TLC = | single spot |

B - Synthesis of 2-butyryloxy-5-[2-(pyrrolidin-1-yl)ethoxy]-p-cymene hydrochloride (B 1132)

16.67 g (0.05 mol) of this oil are dissolved in 180 ml of anhydrous ethyl ether. The solution is saturated with a stream of dry HCl gas (in an ice bath). The crystals formed are filtered off, washed with anhydrous ethyl ether and then dried over phosphorus pentoxide at 50° C.

This gives 12.18 g of beige crystals (yield of crude product=65.8%).

After recrystallization from isopropanol, 10.04 g of slightly beige crystals are isolated.

| | |
|---|---|
| Yield after recrystallization = | 54.3% |
| M.p.$_{KB}$ = | 189–190° C. |
| TBAH titer = | 97.8% |
| AgNO$_3$ titer = | 97% |
| GC purity = | 99.8% |

IR = consistent with the proposed structure
NMR = consistent with the proposed structure
Karl Fischer (water determination) = 0.2%
TLC = single spot The hydrochlorides mentioned in the summary table below were prepared by following the same procedure as in Example 5:

SUMMARY TABLE

| Code no. | n | Empirical formula (MW) | Yield % | M.p.$_{KB}$ °C. (recryst. solvent) |
|---|---|---|---|---|
| B 1125 | 1 | C$_{19}$H$_{30}$ClNO$_3$ (355.91) | 51.2 | 177–178 |
| B 1132 | 2 | C$_{20}$H$_{32}$ClNO$_3$ (369.94) | 54.3 | 189–190 (IPA) |
| B 1131 | 4 | C$_{22}$H$_{36}$ClNO$_3$ (397.99) | 50 | 156–157 (IPA) |
| B 1134 | 8 | C$_{26}$H$_{44}$ClNO$_3$ (454.10) | 45.4 | 148–149 (IPA) |

The products according to the invention were studied for their toxicity and their pharmacological properties.

1. Toxicity

The following 50% lethal doses were obtained after oral administration (p.o.) and intravenous administration (i.v.) of the substances to mice.

The results obtained are collated in Table I.

TABLE I

| Substance | LD$_{50}$ - mg/kg | |
|---|---|---|
| | p.o. | i.v. |
| B 1007 | 330 | 75 |
| B 1024 | 100 | 18 |
| B 1058 | 80 | 17 |
| B 1125 | ≃300 | ND* |
| B 1131 | ≃550 | ND* |
| B 1132 | ≃500 | ND* |
| B 1134 | ≃400 | 36 |
| Thymoxamine | 300 | 72.5 |

*ND: not determined

2. Pharmacological properties 2.1. - In vitro α-adrenolytic activity

This was studied on the ductus deferens of rats and on the urethra of rabbits.

Principle of the measurement:

Norepinephrine causes contractions of the isolated ductus deferens of rats and the isolated urethra of rabbits. The presence of α-blocking substances in a bath containing the organ antagonizes these contractions; the use of increasing concentrations of α-blocking substances makes it possible to calculate:

the pA$_2$ of the compounds on the ductus deferens of rats, the pA$_2$ being the negative logarithm of that molar concentration of the product in the presence of which the concentration of norepinephrine has to be doubled in order to obtain the same effect as in the absence of the product; and the pD'$_2$ of the compounds on the urethra of rabbits, the pD'$_2$ being the negative logarithm of that molar concentration of the product in the presence of which the contraction-inducing activity of norepinephrine is halved.

Results:

The results obtained are collated in Table II.

TABLE II

| | α-Blocking action towards norepinephrine | |
|---|---|---|
| PRODUCT | on isolated ductus deferens pA$_2$ | on isolated urethra pD'$_2$ |
| B 1007 | 6.74 | 6.88 |
| B 1024 | 6.98 | 6.38 |
| B 1058 | 7.18 | 6.69 |
| B 1125 | 7.14 | 6.25 |
| B 1131 | 6.98 | 6.12 |
| B 1132 | 7.35 | 6.0 |
| B 1134 | 6.57 | 6.23 |
| Thymoxamine | 7.25 | 7.03 |

These results show an interesting α-blocking activity for the products tested.

2.2. - In vivo adrenolytic activity 2.2.1. In rats

Principle of the measurement:

Norepinephrine injected intravenously in high doses causes the death of 100% of the animals within 15 minutes of being injected. The cause of death is pulmonary edema due to the arterial hypertension induced by stimulation of the adrenergic receptors. The oral administration of α-adrenolytic substances before-hand enables the toxicity of norepinephrine to be reduced. The products are administered orally at times varying between 30 minutes and 6 hours before the intravenous injection (i.v.) of norepinephrine (0.4 mg/kg).

Results:

The results obtained are collated in Table III.

TABLE III

| PRODUCT | Dose p.o. mg/kg | % protection against death | Time of administration of the products before i.v. |
|---|---|---|---|
| B 1007 | 50 | 60 | 30 min |
| B 1024 | 25 | 70 | 30 min |
| B 1058 | 50 | 90 | 30 min |
| B 1125 | 25 | 60 | 30 min |
| B 1131 | 50 | 60 | 30 min |
| B 1132 | 50 | 90 | 30 min |
| B 1134 | 100 | 100 | 4 h |
| Thymoxamine | 50 | 80 | 30 min |

These results show that the products tested provide effective protection against the toxicity of norepinephrine.

2.2.2. In anesthetized rabbits

The "in vivo" α-blocking activity in terms of the urethral and vascular pressures in anesthetized rabbits was investigated by intravenous administration of the products B 1007, B 1024, B 1058, B 1125 and B 1134.

Principle of the measurement:

The intravenous injection of norepinephrine causes a dose-dependent increase in the arterial and urethral pressures in rabbits. α-Blocking substances injected intravenously antagonize these pressure increases as a function of dose. The 50% inhibitory dose ($ID_{50}$), defined as being the dose of product which causes a 50% increase in the effects of norepinephrine on the arterial and urethral pressures, is calculated.

Results:

The results obtained are collated in Table IV.

TABLE IV

| | $ID_{50}$ (mg/kg) with regard to | |
|---|---|---|
| PRODUCT | arterial hypertension | urethral hypertension |
| B 1007 | 7.63 | 0.34 |
| B 1024 | 4.14 | 0.23 |
| B 1058 | 1.22 | 0.13 |
| B 1125 | 5.95 | 0.36 |
| B 1134 | 6.17 | 0.48 |
| Thymoxamine | 2.72 | 0.5 |

These results show that the products tested antagonize the increase in urethral pressure at much lower doses than are necessary to antagonize the increase in arterial pressure.

2.2.3. Urethral specificity in anesthetized dogs

The effect of products B 1007, B 1024, B 1125 and B 1134, injected intravenously, on the neurogenic urethral hypertension and the arterial pressure was investigated on anesthetized dogs.

Principle of the measurement:

Electrical stimulation of the hypogastric nerve causes an increase in the urethral pressure by releasing norepinephrine from the sympathetic fibers of the nerve.

α-Blocking substances antagonize these increases in urethral pressure as a function of dose and cause arterial hypotension through a blocking action on the vascular receptors.

The dose which causes a 50% inhibition of the effects of stimulation of the hypogastric nerve on the urethral pressure ($ID_{50}$) and the dose which causes a 20% arterial hypotension ($ED_{20}$) are calculated.

Results:

The results obtained are collated in Table V.

TABLE V

| PRODUCT | Arterial hypotension $ED_{20}$ - mg/kg | Neurogenic urethral hypertension $ID_{50}$ - mg/kg |
|---|---|---|
| B 1007 | 2 | 0.35 |
| B 1024 | 8 | 0.07 |
| B 1125 | 12 | 0.09 |
| B 1134 | 30 | 0.11 |
| Thymoxamine | 0.27 | 0.09 |

These results show that the products tested antagonize the increase in urethral pressure induced by stimulation of the hypogastric nerve at doses very much lower than those which cause a hypotensive vascular effect.

The toxicological and pharmacological experiments show that the products according to the invention can be administered, orally or by injection, as drugs in functional urethral pathologies dependent on a sympathetic mechanism.

What is claimed is:

1. A compound of the formula

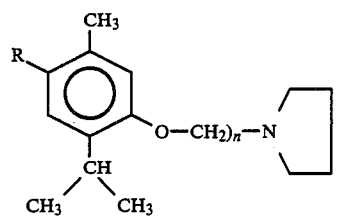

in which R is selected from the group consisting of H, OH, —OCOCH$_3$ and —O—CO—(CH$_2$)$_n$—CH$_3$, in which n is from 1 to 8, and pharmaceutically acceptable acid addition salts thereof.

2. The compound according to claim 1, wherein n is selected from the group consisting of 1, 4, and 8.

3. A pharmaceutical composition for blocking alpha-receptors, which comprises a compound of the formula

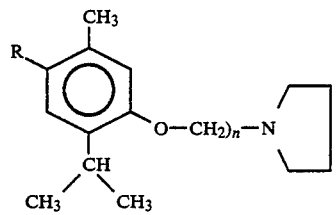

in which R is selected from the group consisting of H, OH, —OCOCH$_3$, and —O—CO—(CH$_2$)$_n$—CH$_3$, in which n is from 1 to 8, and pharmaceutically acceptable acid addition salts thereof, together with a pharmaceutically acceptable carrier.

4. A method of blocking alpha-receptors, which comprises administering to a host a compound of the formula

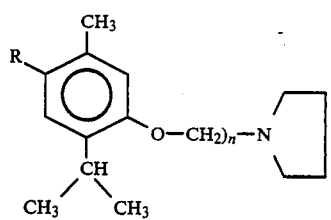
in which R is selected from the group consisting of H, OH, —OCOCH$_3$, and —O—CO—(CH$_2$)$_n$—CH$_3$, in which n is from 1 to 8, along with a pharmaceutically acceptable carrier in an amount effective to block the host's alpha-receptors.
5. The method according to claim 4, wherein n is selected from the group consisting of 1, 4 and 8.
* * * * *